United States Patent
Kopperschmidt et al.

(10) Patent No.: US 10,940,258 B2
(45) Date of Patent: Mar. 9, 2021

(54) DIALYSIS DEVICE HAVING MEANS FOR RECOGNIZING A SHUNT RECIRCULATION

(71) Applicant: FRESENIUS MEDICAL CARE DEUTSCHLAND GMBH, Bad Homburg (DE)

(72) Inventors: Pascal Kopperschmidt, Dittelbrunn (DE); Alfred Gagel, Litzendorf (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 173 days.

(21) Appl. No.: 16/064,220

(22) PCT Filed: Dec. 23, 2016

(86) PCT No.: PCT/EP2016/002181
§ 371 (c)(1),
(2) Date: Dec. 4, 2018

(87) PCT Pub. No.: WO2017/108195
PCT Pub. Date: Jun. 29, 2017

(65) Prior Publication Data
US 2019/0083694 A1 Mar. 21, 2019

(30) Foreign Application Priority Data
Dec. 23, 2015 (DE) ................. 10 2015 016 854.1

(51) Int. Cl.
*A61M 1/34* (2006.01)
*A61M 1/36* (2006.01)

(52) U.S. Cl.
CPC .......... *A61M 1/3403* (2014.02); *A61M 1/342* (2013.01); *A61M 1/3413* (2013.01);
(Continued)

(58) Field of Classification Search
CPC .. A61M 1/3403; A61M 1/3413; A61M 1/342; A61M 1/3431; A61M 1/3437;
(Continued)

(56) References Cited

U.S. PATENT DOCUMENTS

| | | | |
|---|---|---|---|
| 2010/0276367 A1* | 11/2010 | Zhang | A61M 1/342 210/647 |
| 2014/0083943 A1 | 3/2014 | Nuernberger | |

FOREIGN PATENT DOCUMENTS

| | | |
|---|---|---|
| DE | 10218846 | 9/2003 |
| DE | 102013103221 | 10/2014 |

(Continued)

*Primary Examiner* — Dirk R Bass
(74) *Attorney, Agent, or Firm* — Jacobson Holman PLLC

(57) ABSTRACT

A dialysis device having an extracorporeal blood circuit which has an arterial line having a blood pump and an arterial needle for connection to a patient, a venous line having a venous needle for connection to a patient and a dialyzer arranged between the arterial line and the venous line and having a blood chamber and a dialysis fluid chamber is provided. The dialysis device furthermore has a control unit and an extracorporeal blood pressure sensor which is arranged at the suction side of the blood pump. The control unit is configured such that a signal output takes place which indicates the presence of recirculation when a change in the signal of the sensor following a trigger event exceeds a threshold value.

10 Claims, 3 Drawing Sheets

(52) U.S. Cl.
CPC ........ *A61M 1/3431* (2014.02); *A61M 1/3437* (2014.02); *A61M 1/3609* (2014.02); *A61M 1/3639* (2013.01); *A61M 1/3658* (2014.02); *A61M 2205/3344* (2013.01); *A61M 2205/3351* (2013.01)

(58) Field of Classification Search
CPC .............. A61M 1/3609; A61M 1/3639; A61M 1/3658; A61M 2205/3344; A61M 2205/3351
See application file for complete search history.

(56) References Cited

FOREIGN PATENT DOCUMENTS

| | | |
|---|---|---|
| DE | 102014111665 | 2/2016 |
| EP | 1790363 | 3/2010 |
| EP | 2238996 | 10/2010 |
| WO | WO 98/17334 | 4/1998 |

* cited by examiner

DIALYSIS DEVICE HAVING MEANS FOR RECOGNIZING A SHUNT RECIRCULATION

The invention relates to a dialysis device having means for recognizing a shunt recirculation.

BACKGROUND OF THE INVENTION

1. Field of the Invention

If the arterial needle and the venous needle of the extracorporeal blood circuit of a dialysis device is applied in the region of a shunt (an artificially created shunt between an artery and a vein in the patient for a better performability of a dialysis treatment), shunt recirculation can take place, wherein a portion of the purified blood which is reinfused into the vessel of the patient through the venous needle again moves directly into the extracorporeal blood circuit through the arterial needle. Such shunt recirculation is unwanted since the dialysis efficiency is lowered. It is desirable against this background to be able to detect the presence of shunt recirculation.

2. Description of the Related Art

A dialysis device is known from EP 1 790 363 B1 with which a detection of shunt recirculation can take place. This device has hematocrit sensors in the arterial line and in the venous line of the extracorporeal blood circuit. Provision is made for the detection of shunt recirculation to generate a peak in the hematocrit value of the extracorporeally conducted blood by a temporary elevation of the ultrafiltration rate at the dialyzer. This peak is then recognized at the venous hematocrit sensor. If a corresponding peak is also recognized in the correct time offset at the arterial hematocrit sensor, a conclusion on shunt recirculation is drawn.

SUMMARY OF THE INVENTION

It is the object of the invention to provide a dialysis device with which the detection of shunt recirculation can take place in a simpler manner.

Against this background, the invention relates to a dialysis device having an extracorporeal blood circuit which has an arterial line having a blood pump and an arterial needle for connection to a patient, a venous line having a venous needle for connection to a patient and a dialyzer arranged between the arterial line and the venous line and having a blood chamber and a dialysis fluid chamber, wherein the dialysis device furthermore has a control unit. Provision is made in accordance with the invention that the dialysis device furthermore has an extracorporeal blood pressure sensor which is arranged at the suction side of the blood pump and that the control unit is configured such that a signal output takes place which indicates the presence of recirculation when a change in the signal of the sensor following a trigger event exceeds a threshold value.

In comparison with the system known from EP 1 790 363 B1, a more complex measurement of the hematocrit value can be dispensed with and the determination can take place only using the arterial pressure sensor anyway present in the device. A measurement in the venous line or at the pressure side of the pump is not necessary.

In an embodiment, the trigger event is a temporary thickening or thinning of the blood conducted at the pressure side of the blood pump in the extracorporeal blood circuit. A temporary change of the blood viscosity occurs due to the temporary thickening or thinning of the blood. If blood portions having a changed blood viscosity are recirculated in the shunt and sucked into the extracorporeal blood circuit again after reinfusion to the patient, the resulting temporary change of the flow resistance at the venous needle effects a change of the extracorporeal blood pressure on the suction side of the pump. This change can be detected by the sensor.

In an embodiment, the dialysis device furthermore has a dilution system having a dilution line opening into the extracorporeal blood circuit and having a dilution pump, wherein the control unit is configured such that the trigger event is triggered by a control of the dilution pump.

In an embodiment, the control unit is configured such that the trigger event is triggered by a temporary reduction of the pump power or by a deactivation of the dilution pump.

In an embodiment, the dilution system is a post-dilution system and the dilution line opens into the venous line. On a use of a post-dilution system, a high sensitivity can be achieved with the detection of shunt recirculation.

A temporary reduction of the pump power or a deactivation of the dilution pump results in a temporary thickening of the extracorporeal blood with post-dilution. With pre-dilution, the converse effect normally occurs, which is due to a balancing between substitution and filtration. For a stop of pre-dilution normally results in a stop of filtration so that a diluted bolus results since the blood then runs through the dialyzer without being filtered. A temporary thinning of the blood can also be achieved independently of the selection of pre-dilution or post-dilution by a temporary increase in pump power of a dilution pump. This can be achieved, for example, by means of an additional dilution pump. The signal measured at the arterial sensor in the case of recirculation on a thickening of the blood can be more pronounced due to the non-linear relationship than on a dilution of the blood.

The dialysis device in accordance with the invention in this embodiment is suitable for use as part of a hemo(dia)filtration treatment, wherein the fluid quantity removed in the dialyzer from the blood is substituted by pre-dilution or post-dilution.

In an embodiment, the dialysis device furthermore has an ultrafiltration pump which is connected to the dialysis fluid chamber at the suction side, wherein the control unit is configured such that the trigger event is triggered by a control of the ultrafiltration pump. A temporary reduction of the pump power of the ultrafiltration pump effects a temporary reduction of the transmembrane pressure in the dialyzer, which produces a temporary reduction of the fluid flow from the blood and thus a temporary dilution of the extracorporeal blood. Conversely, a temporary increase in the pump power produces a temporary thickening of the blood.

In an embodiment, the control unit is configured such that the trigger event is triggered by a temporary increase in the pump power of the ultrafiltration pump. As already stated further above, the signal measured at the arterial sensor in the case of recirculation on a thickening of the blood can be more pronounced due to the non-linear relationship than on a dilution of the blood.

In an embodiment, the dialysis device in accordance with the invention is suitable for use as part of a hemodialysis treatment in which no pre-dilution or post-dilution takes place.

In an embodiment, the control unit is configured such that the signal value of the sensor is stored as a starting value directly before the occurrence of the trigger event, such that the maximum or minimum signal value of the sensor during a measurement phase after occurrence of the trigger event is stored as a peak value and such that the change in the signal corresponds to the difference between the starting value and the peak value.

In an embodiment, the control unit is configured such that the duration of the measurement phase corresponds at least to the duration of the trigger event and/or such that the measurement phase starts at a time offset from the trigger event.

In an embodiment, the control unit is configured such that the integral of the difference between the starting value and signal values determined during the measurement phase is determined and such that a signal output takes place on the basis of this integral which indicates the degree of recirculation.

The invention furthermore relates to a method of recognizing shunt recirculation during a dialysis treatment using a dialysis device in accordance with the invention, wherein a signal output takes place which indicates the presence of recirculation when a change in the signal of the sensor following a trigger event exceeds a threshold value.

BRIEF DESCRIPTION OF THE DRAWINGS

Further details and advantages of the invention result from the following embodiment shown with reference to the Figures. There are shown in the Figures.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
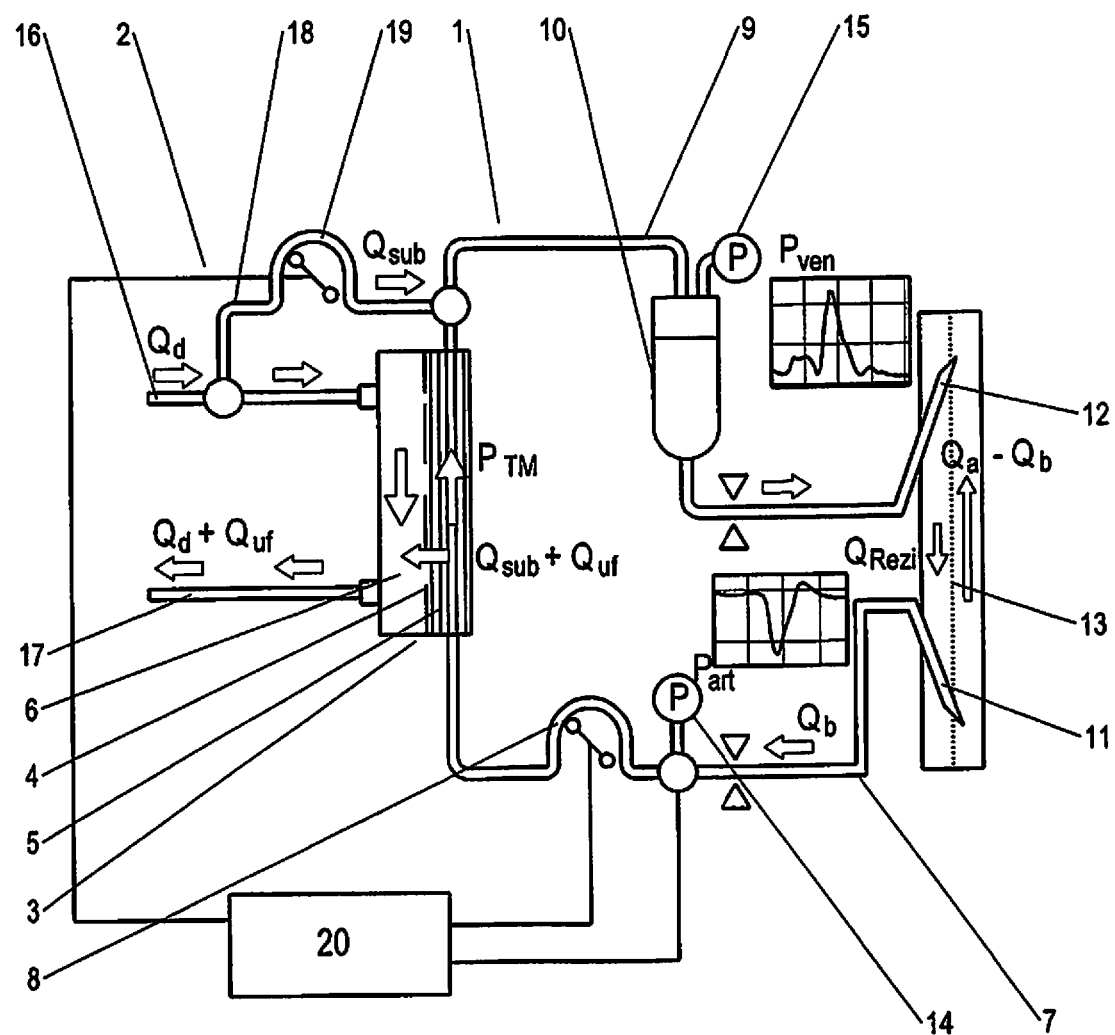
FIG. 1: a schematic representation of a dialysis device in accordance with the invention.

A first embodiment of a dialysis device in accordance with the invention is shown schematically in FIG. 1.

The dialysis device comprises an extracorporeal blood circuit 1 and a dialysis fluid circuit 2 which come into contact with one another at a dialyzer 3. The dialyzer 3 comprises a semipermeable membrane 4 which separates a blood chamber 5, which forms a part of the extracorporeal blood circuit 1, and a dialysis fluid chamber 6, which forms a part of the dialysis fluid circuit 2, from one another. The flow directions of the blood and of the dialysis fluid in the different chambers 5 and 6 of the dialyzer 3 are of opposite directions. The flow directions in the circuits are indicated by arrows in the Figure.

A blood pump 8 is located in the arterial blood line 7 and a drip chamber 10 is located in the venous blood line 9. The arterial needle and the venous needle for connection to the patient are marked by the reference numerals 11 and 12. The vessel of the patient which is in the region of the shunt is marked by reference numeral 13.

An arterial pressure sensor 14 is located at the suction side of the blood pump 8 and a venous pressure sensor 15 is located at the venous drip chamber 10.

The feed line 16 of the dialysis fluid circuit is connected to a dialysis fluid source. The return line 17 of the dialysis fluid circuit is connected to a drain. A post-dilution line 18 in which a dilution pump 19 is arranged branches off from the feed line 16. The post-dilution line 18 opens between the dialyzer 3 and the drip chamber 10 into the venous line 9.

The dialysis device furthermore has a control unit 20 which is at least connected to the blood pump 8, to the arterial pressure sensor 14 and to the dilution pump 19.

The blood in the dialyzer 3 is thickened by the filtration rate $Q_{tm}=Q_{uf}+Q_{sub}$ as part of a post-H(D)F treatment carried out at the device shown. The blood from the venous drip chamber 10 is diluted by the flow $Q_{sub}$ of the substituate or post-dilution pump 19 back to the value of the hematocrit at the dialyzer inlet ($Q_{uf}$ is negligible here).

As soon as the substituate or post-dilution pump 19 stops in H(D)F treatments, a hemobolus (temporary time change of the hematocrit with respect to the stationary state) runs through the venous hose system 9. The thickened blood is flushed out and flows via the venous needle 12 back into the shunt 13 of the patient. The changing blood viscosity causes a peak in the venous pressure which arises due to the hemodynamic pressure drop in the needle.

Figure 2:
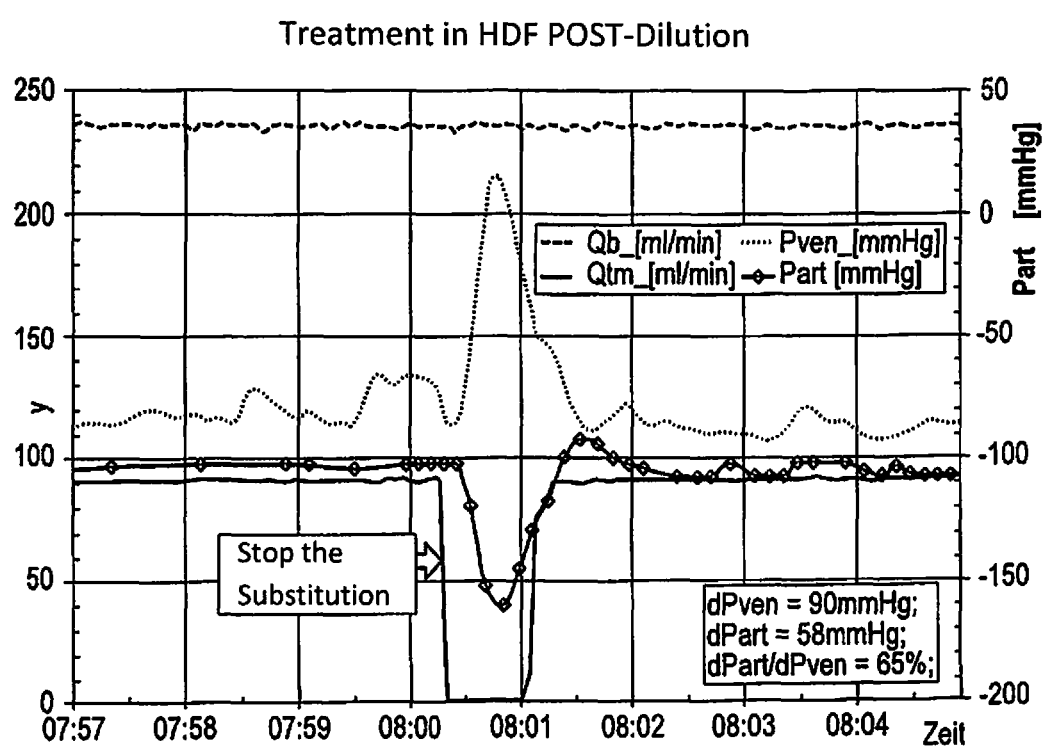
FIG. 2: a representation of the time curves of arterial and venous pressure signals on a suspension of the post-dilution during an HDF treatment with shunt recirculation present.

The time curve of the venous pressure was determined as part of an exemplary measurement and is shown in FIG. 2.

A portion of the thickened blood moves via the recirculation flow $Q_{Rezi}$ in the shunt 13 back to the arterial needle 11 and is there sucked into the arterial needle 11 with the blood flow $Q_b$. The hematocrit of the arterial inlet blood changes by the mixing, whereby a peak arises in the arterial pressure at higher or lower negative pressures. The height and the area below the arterial pressure peak can serve as a measure for the recirculation.

The venous and arterial pressure peaks shown in FIG. 2 arise through dynamic pressure drops in the respective needle 11 or 12 which are caused by the flow of the thickened blood. Since the blood volume in the shunt 13 is very small, the two peaks occur practically simultaneously. The curve shapes of the two mirror inverted signals are similar (without noise) to one another. Both the coincidence of the two peaks and the similarity of the curve shapes of the two pressure signals are therefore helpful criteria for recognizing recirculation.

The evaluation of the signals by the routine stored in the control unit 20, which serves to recognize increased shunt recirculation, can take place as follows, for example, in the embodiment shown.

The arterial pressure $P_{art,Start}$ can be stored directly before the trigger time. After the trigger time, the following difference of the arterial pressure $\Delta P_{art}$ can be calculated with the aid of the current arterial pressure $P_{art}$.

$$\Delta P_{art}(t) = P_{art}(t) - P_{art,Start} \tag{1}$$

The peak in the pressure difference can subsequently be determined as follows, wherein the trigger time is the start of the routine with $t=0$, $V_b=0$ and $\Delta P_{art,Peak}=0$.

$$\Delta P_{art,Peak,new} = \begin{cases} P_{art}(t) - P_{art,Start} & \text{if} \quad \Delta P_{art,Peak,alt} > P_{art}(t) - P_{art,Start} \quad \text{on thinkening} \\ \Delta P_{art,Peak,alt} & \text{else} \\ P_{art}(t) - P_{art,Start} & \text{if} \quad \Delta P_{art,Peak,alt} < P_{art}(t) - P_{art,Start} \quad \text{on thinning} \end{cases} \tag{2}$$

The peak search can in this respect be limited to a time (t–) interval or to a conveyed blood volume ($V_b$–) interval in which the expected peak has to occur.

In this respect, a delay is preferably taken into account in the following manner, on the one hand, which the blood requires to move from the dialyzer up to the venous needle.

$$t_{delay} = V_{SS,ven}/Q_b \quad (3)$$

In this respect, $t_{delay}$ represents the delay time measured in minutes, for example, which elapses until the peak can occur. $V_{SS,ven}$ represents the delay volume measured in mL, for example, which can be equated, for example, with the volume of the venous hose system. Finally, $Q_b$ represents the blood flow expressed in ml/min, for example.

In this respect, on the other hand, an active duration in which the peak has to occur is taken into account in the following manner.

$$t_{Peak} = \alpha * V_{dialyzer}/Q_b \quad (3)$$

In this respect, $t_{Peak}$ represents the time interval expressed in minutes, for example, in which the peak has to occur. $V_{dialyzer}$ furthermore represents the conveyed blood volume in which the peak has to occur. It can, for example, be equated with the volume of the blood chamber 5 of the dialyzer 3 and can be expressed in mL. The variable a describes an additional weighting factor which takes into account that, in a post-H(D)F treatment, the blood with the highest thickening is present at the dialyzer outlet while, with pre-H(D)F, the blood with the highest thinning is present at the dialyzer inlet. For example, with a typical post-H(D)F, the delay volume can be in the order of magnitude of 55 mL and the blood volume in the active duration can be in the order of magnitude of 65 mL.

It can be demanded in the further consequence that the peak in the pressure difference exceeds a threshold value $\Delta P_{art,Peak,Limit}$ so that the presence of increased recirculation can be assumed. The threshold value $\Delta P_{art,Peak,Limit}$ can, for example, be defined in dependence on the filtration fraction $FF=(Q_{uf}+Q_{sub})/Q_b$ because the thickening or thinning of the blood also increases as the filtration fraction FF increases.

For example, a relationship advantageous in a post-H(D)F treatment is shown in equation (4).

$$\Delta P_{art,Peak,Limit} = 10 \text{ mmHg} * \left(1 + \frac{FF - 15\%}{35\%}\right) \text{ for } FF \geq 15\% \quad (4)$$

In this case, no evaluation would be carried out at FF<15%.

A check of the peak shape in the arterial pressure can subsequently be carried out. It can, for example, be expected after the maximum peak height $\Delta P_{art,Peak}$ has been detected that the pressure difference $\Delta P_{art}(t)$ again strives toward zero or at least again falls below a specific threshold.

As part of the concept in accordance with the invention, the fluctuation range $\sigma_{Part}$ of the undisturbed arterial pressure can furthermore be considered. It is assumed, for example, that the peak height $\Delta P_{art,Peak}$ has to be considerably larger than the fluctuation range apart of the undisturbed arterial pressure $P_{art}$.

$$\left|\frac{\Delta P_{art,Peak}}{\sigma_{art}}\right| \geq k \quad (5)$$

It can be demanded in an embodiment in this respect that with post-H(D)F the ratio has to amount to k>3.0 . . . 4.0.

Provision can optionally be made that if increased recirculation has been recognized in a measurement, it is repeated to verify the first result. If both results were only slightly positive, it can furthermore also be attempted to confirm the result with a third measurement or with further measurements.

Furthermore, in the evaluation a clearance $Cl_{OCM}$ measured by OCM (online clearance measurement) can optionally also be considered. If the clearance $Cl_{OCM}$ or, better, the relationships $Cl_{OCM}/Q_b$ or $Cl_{OCM}*t/V_b$ are considerably lower than a usual threshold value, this can likewise be used in an embodiment as an indication of a high shunt recirculation and can also be taken into account in the evaluation of the result of the arterial pressure peak.

A warning for the user that increased shunt recirculation is present can optionally take place directly after the evaluation of the results. Alternatively, the report output can also take place later, for example after the acknowledgment of the report output that the treatment goal has been reached.

The inventive ideal does not necessarily include the claim of directly measuring the recirculation flow. It is rather the goal to recognize unusually high recirculation and to report it to the user. Downstream examinations can thus be triggered in which e.g. the recirculation flow can be determined exactly with the aid of a dedicated process.

The method is particularly sensitive in post-H(D)F treatments in a device in accordance with FIG. 1. Due to the non-linear relationship, the blood viscosity is as a rule changed more by thickening of the blood than by the dilution at pre-H(D)F.

However, the use as part of a pre-H(D)F treatment is also conceivable in an alternative embodiment. In this case, the blood is diluted by the substitution rate $Q_{sub}$ upstream of the dialyzer. The blood is thickened again by the filtration rate $Q_{tm}=Q_{uf}+Q_{sub}$ in the dialyzer so that the hematocrit at the dialyzer outlet again corresponds to the original value ($Q_{uf}$ is negligible here).

No additional hardware components are preferably required in the dialysis device and the sensors and actuators present as standard are sufficient for these measures contemplated as part of the invention.

Figure 3:
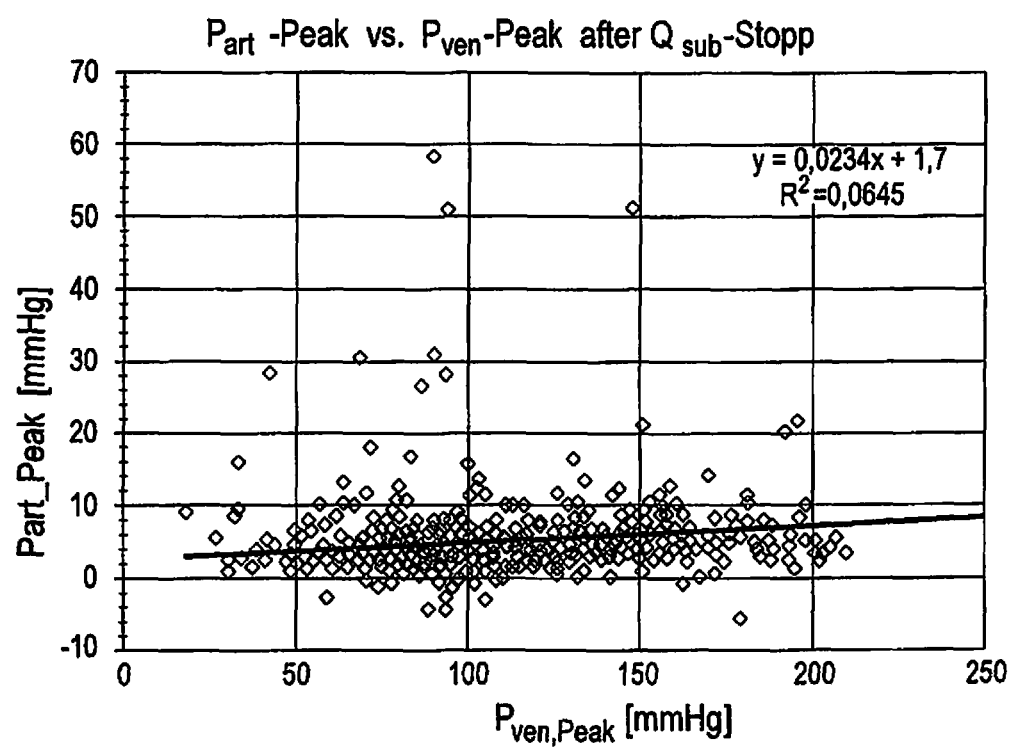
FIG. 3: a representation of the lack of correlation of the arterial and venous pressure signals without shunt recirculation.

A determination of the height or of the integral surface of the venous pressure peak is not necessary in principle as part of the invention because the height of the peak in the arterial pressure does not depend on the peak height of the venous pressure as long as no recirculation is present. Cf. in this connection the representation of FIG. 3, in which peak heights in the arterial pressure are entered against peak heights in the venous pressure which were caused by hemoboli as a result of stops of the substitution pump in post-HDF treatments (N=967). It can only be presumed that increased recirculation is present when the height of the arterial peak is outside the scatter band range.

The invention can primarily be used in pre-H(D)F treatments and post-H(D)F treatments. In HD treatments, the thickening of the blood can e.g. be produced by a brief high UF rate $Q_{uf}$.

A system-induced, significant change of the substitution rate can be used as the condition for the triggering of the trigger event. A particularly high change is represented, for example, by a stop or restart of the substitution pump, which can be induced in any treatment, for example by an event-controlled pressure holding test.

In summary, it results that the shown embodiment of the invention provides a dialysis device having the capability of recognizing recirculation in the shunt as part of a post-HDF treatment. A hemobolus is produced in the extracorporeal blood circuit by switching off the (pre or post) substitution pump since the ultrafiltration pump continues to thicken the blood. This bolus first produces a pressure peak on the venous side. If fistula recirculation is now present, the bolus migrates almost immediately through the patient to the arterial side of the extracorporeal blood circuit. A conclusion is drawn on recirculation due to the simultaneity of the peaks. With respect to EP 1 790 363 B1, the present invention is directed to recognizing the recirculation completely without the determination of the venous pressure. For this purpose, the arterial peak is put into temporal relation with the event which causes the venous peak, that is, in particular the switching off of the substitution pump. In addition, the height of the recirculation is not necessarily determined. Instead, it is also possible—in particular with very high recirculation-only to draw a conclusion on the fact of recirculation on the basis of the arterial peak.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A dialysis device comprising an extracorporeal blood circuit which has an arterial line having a blood pump and an arterial needle for connection to a patient, a venous line having a venous needle for connection to a patient and a dialyzer arranged between the arterial line and the venous line and having a blood chamber and a dialysis fluid chamber, said dialysis device further comprising a control unit, a dilution system having a dilution line opening into the extracorporeal blood circuit and having a dilution pump, and an extracorporeal blood pressure sensor which is arranged at a suction side of the blood pump, said control unit being configured such that a signal output takes place which indicates the presence of recirculation when a change in a signal value of the blood pressure sensor following a trigger event exceeds a threshold value, said trigger event being a temporary thickening of the blood conducted in the extracorporeal blood circuit at a pressure side of the blood pump, said control unit being configured such that the trigger event is triggered by a control of the dilution pump for said temporary thickening of the blood.

2. The dialysis device in accordance with claim 1, wherein the control unit is configured such that the trigger event is triggered by a temporary reduction of the pump power or by a deactivation of the dilution pump.

3. The dialysis device in accordance with claim 1, wherein the dilution system is a post-dilution system and the dilution line opens into the venous line.

4. The dialysis device in accordance with claim 1, wherein the control unit is configured such that the signal value of the sensor is stored as a starting value directly before the occurrence of the trigger event, such that the maximum or minimum signal value of the sensor during a measurement phase after occurrence of the trigger event is stored as a peak value and such that the change in the signal value corresponds to the difference between the starting value and the peak value.

5. The dialysis device in accordance with claim 4, wherein the control unit is configured such that a duration of the measurement phase corresponds at least to a duration of the trigger event.

6. The dialysis device in accordance with claim 4, wherein the control unit is configured such that the integral of the difference between the starting value and signal values determined during the measurement phase is determined and such that a signal output takes place on the basis of this integral which indicates the degree of recirculation.

7. The dialysis device in accordance with claim 4, wherein the control unit is configured such that the measurement phase starts at a time offset from the trigger event.

8. The dialysis device in accordance with claim 4, wherein the control unit is configured such that a duration of the measurement phase corresponds at least to a duration of the trigger event and such that the measurement phase starts at a time offset from the trigger event.

9. A dialysis device comprising an extracorporeal blood circuit which has an arterial line having a blood pump and an arterial needle for connection to a patient, a venous line having a venous needle for connection to a patient and a dialyzer arranged between the arterial line and the venous line and having a blood chamber and a dialysis fluid chamber, said dialysis device further comprising a control unit, an extracorporeal blood pressure sensor which is arranged at a suction side of the blood pump, and an ultrafiltration pump in communication with the dialysis fluid chamber at the suction side, said control unit being configured such that a signal output takes place which indicates the presence of recirculation when a change in a signal value of the blood pressure sensor following a trigger event exceeds a threshold value, said trigger event being a temporary thickening of the blood conducted in the extracorporeal blood circuit at a pressure side of the blood pump, wherein the control unit is configured such that the trigger event is triggered by a control of the ultrafiltration pump for said temporary thickening of the blood.

10. The dialysis device in accordance with claim 9, wherein the control unit is configured such that the trigger event is triggered by a temporary increase in the pump power of the ultrafiltration pump.

* * * * *